United States Patent
Choi

(10) Patent No.: US 9,055,897 B2
(45) Date of Patent: Jun. 16, 2015

(54) METHOD AND APPARATUS FOR MEASURING OTOACOUSTIC EMISSION

(75) Inventor: Yong-sun Choi, Yongin-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 817 days.

(21) Appl. No.: 12/905,620

(22) Filed: Oct. 15, 2010

(65) Prior Publication Data

US 2011/0166806 A1 Jul. 7, 2011

(30) Foreign Application Priority Data

Jan. 6, 2010 (KR) .................. 10-2010-0000906

(51) Int. Cl.
*G01N 29/14* (2006.01)
*A61B 5/12* (2006.01)
*A61B 5/00* (2006.01)

(52) U.S. Cl.
CPC .............. *A61B 5/125* (2013.01); *A61B 5/7235* (2013.01)

(58) Field of Classification Search
USPC .............. 702/56, 75, 85; 73/585, 587; 381/60
See application file for complete search history.

(56) References Cited

U.S. PATENT DOCUMENTS 5,792,073 A * 8/1998 Keefe ........................... 600/559
7,054,453 B2 * 5/2006 Causevic et al. ............. 381/94.1

OTHER PUBLICATIONS

Choi, Yong-Sun et al, "Stimulus-frequency otoacoustic emission: Measurements in humans and simulations with an active cochlear model," Journal of the Acoustical Society of America, vol. 123 (5), May 2008, pp. 2651-2669.

* cited by examiner

*Primary Examiner* — John Breene
*Assistant Examiner* — Hien Vo
(74) *Attorney, Agent, or Firm* — Sughrue Mion, PLLC

(57) ABSTRACT

A method of measuring an otoacoustic emission (OAE) is provided. The method comprises generating a frequency OAE graph with N plot lines, by performing frequency sweeping on N signals having different levels, wherein N is a natural number of at least 2; and when there are plot lines that overlap each other in the frequency OAE graph, compensating values of the N plot lines of the frequency OAE graph in a predetermined frequency section including a frequency section where the plot lines overlap each other.

19 Claims, 5 Drawing Sheets

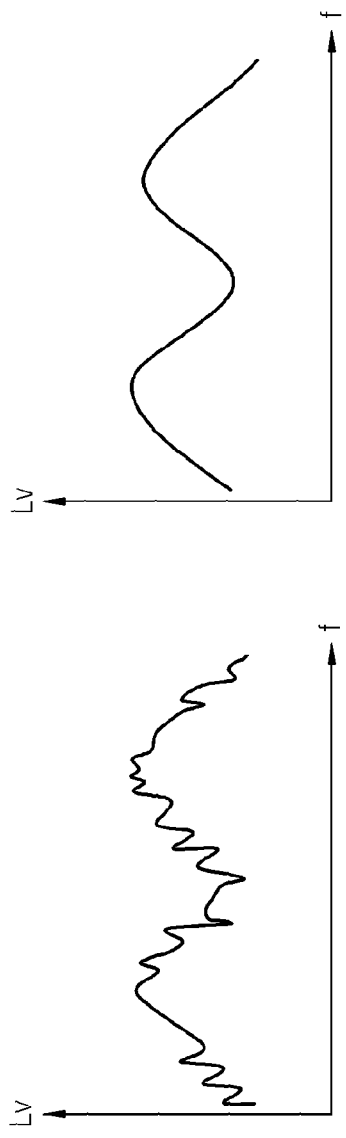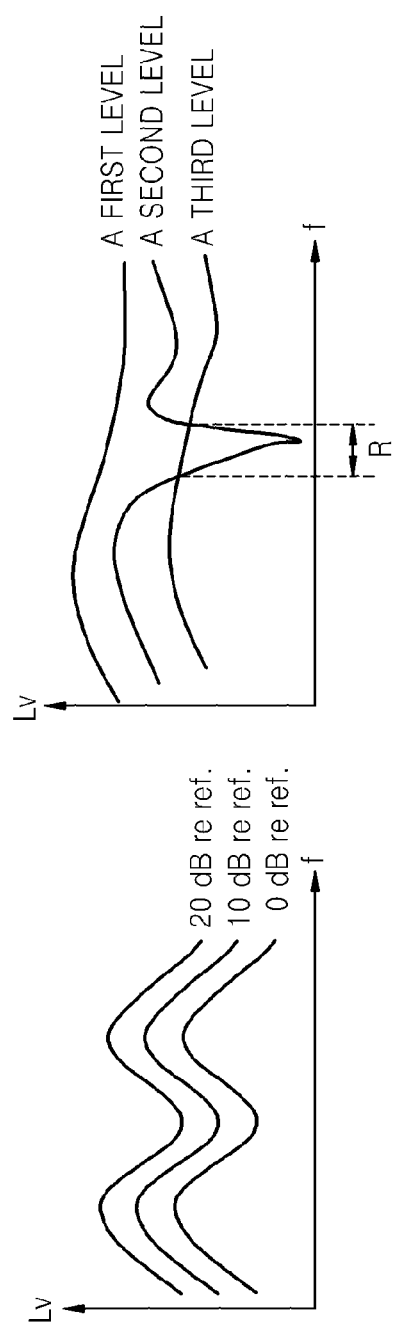

METHOD AND APPARATUS FOR MEASURING OTOACOUSTIC EMISSION

CROSS-REFERENCE TO RELATED PATENT APPLICATION

This application claims priority from Korean Patent Application No. 10-2010-0000906, filed on Jan. 6, 2010, in the Korean Intellectual Property Office, the disclosure of which is incorporated herein in its entirety by reference.

BACKGROUND

1. Field

Methods and apparatuses consistent with the exemplary embodiments relate to measuring an otoacoustic emission (OAE), and more particularly, to a method and apparatus for measuring an OAE, which have a short OAE measuring time and are reliable by minutely measuring only signals in a required section while measuring the OAE.

2. Description of the Related Art

An example of a method of measuring an auditory characteristic includes a pure tone audiometry (PTA) method of measuring a value of the threshold of audibility as a subject responds when a constant reference sound is heard. The PTA method is not convenient for measuring an auditory characteristic in a middle band, and the concentration and selection of the subject affects a result of the PTA method.

On the other hand, a method of measuring an otoacoustic emission (OAE) measures an auditory characteristic without a reaction of a subject. The OAE is sound generated in the ear, i.e., sound energy generated according to an active amplification action of an outer hair cell (OHC) inside a cochlea. Since damage of the OHC largely causes hearing loss, the auditory characteristic of the subject may be measured by measuring a reaction of the OHC according to frequencies and input levels.

Generally, in order to measure the OAE, a signal corresponding to a predetermined frequency and a predetermined input level is transmitted to the subject and the signal received by the ear of the subject is measured. This process is repeated after changing the frequency and the input level of the signal.

When the OAE is measured according to signals having different frequencies but the same input levels, a section in which values of the OAE change remarkably may be generated due to the intrinsic characteristics of the OAE. Alternatively, when the OAE is measured according to signals having the same frequencies but different input levels, a section in which values of the OAE are different from auditory characteristic of the subject may be generated. Accordingly, a reliable method of measuring OAE is required.

Also, unnecessary information is generated when the OAE is measured for all possible combinations of frequencies and input levels so as to measure the OAE in frequencies and input levels in wide ranges.

SUMMARY OF THE EXEMPLARY EMBODIMENTS

The exemplary embodiments provide a method and apparatus for reliably measuring an otoacoustic emission (OAE) by compensating for values of OAEs in a section in which the values change remarkably by performing frequency sweeping and level sweeping together.

The exemplary embodiments also provide a method and apparatus for measuring OAEs, which have a short OAE measuring time and do not generate unnecessary information, by performing level sweeping on frequencies in a section in which values of OAEs according to frequencies change remarkably.

According to an aspect of the exemplary embodiments, there is provided a method of measuring an otoacoustic emission (OAE), including: generating a frequency OAE graph with N plot lines by performing frequency sweeping on N signals having different levels, wherein N is a natural number of at least 2, and when there are plot lines that overlap each other in the frequency OAE graph, compensating values of the N plot lines of the frequency OAE graph in a predetermined frequency section including a frequency section where the plot lines overlap each other.

The N signals may have regular level intervals. The method may further include liftering a low band signal of the frequency OAE graph in a quefrency domain. The compensating of the values of the N plot lines may include: selecting a frequency in the frequency section where the plot lines overlap each other; generating a level OAE graph by performing level sweeping on a signal corresponding to the selected frequency; compensating an OAE value in a section that is out of a reference pattern in the level OAE graph; and compensating values of the N plot lines of the frequency OAE graph by using the level OAE graph having the compensated OAE value.

The selecting of the frequency may include selecting a middle frequency in the frequency section where the plot lines overlap each other. The selecting of the frequency may include selecting a frequency at a point where a difference between OAE values of the plot lines that overlap each other is the largest, wherein the point may be in the frequency section where the plot lines overlap each other.

The compensating of the values of the N plot lines of the frequency OAE graph by using the level OAE graph having the compensated OAE value may include: compensating the values of the N plot lines at the selected frequency by using the level OAE graph having the compensated OAE value, and compensating OAE values in the predetermined frequency section that is larger than the frequency section where the plot lines overlap each other, by using the values of the N plot lines at the selected frequency.

The compensating of the OAE value in the section that is out of the reference pattern may include: detecting the section that is out of the reference pattern in the level OAE graph, and compensating values of a plot line of the level OAE graph in the detected section according to the reference pattern. The detecting of the section that is out of the reference pattern may include detecting a section wherein the values of the plot line of the level OAE graph may not be constants and a gradient of the plot line of the level OAE graph may be nonlinear.

According to another aspect of the exemplary embodiments, there is provided an apparatus for measuring an otoacoustic emission (OAE), including: a frequency OAE measurer which generates a frequency OAE graph with N plot lines by performing frequency sweeping on N signals having different levels, wherein N is a natural number of at least 2, and a frequency OAE compensator, which, when there are plot lines that overlap each other in the frequency OAE graph, compensating values of the N plot lines of the frequency OAE graph in a predetermined frequency section including a frequency section where the plot lines overlap each other.

According to another aspect of the exemplary embodiments, there is provided a computer readable recording medium having recorded thereon a program for executing a method of measuring an otoacoustic emission (OAE), the method including: generating an frequency OAE graph with N plot lines by performing frequency sweeping on N signals having different levels, wherein N is a natural number of at least 2, and when there are plot lines that overlap each other in the frequency OAE graph, compensating values of the N plot lines of the frequency OAE graph in a predetermined frequency section including a frequency section where the plot lines overlap each other.

BRIEF DESCRIPTION OF THE DRAWINGS

The above and other features of the exemplary embodiments will become more apparent by describing in detail exemplary embodiments thereof with reference to the attached drawings in which:

FIG. 3 are frequency OAE graphs before liftering a low band signal and after liftering the low band signal, respectively;

FIG. 4 are OAE graphs that are generated by performing frequency sweeping respectively in an ideal situation and an actual situation;

DETAILED DESCRIPTION OF THE EXEMPLARY EMBODIMENTS

Hereinafter, the exemplary embodiments will be described more fully with reference to the accompanying drawings, in which exemplary embodiments are shown.

Figure 1:
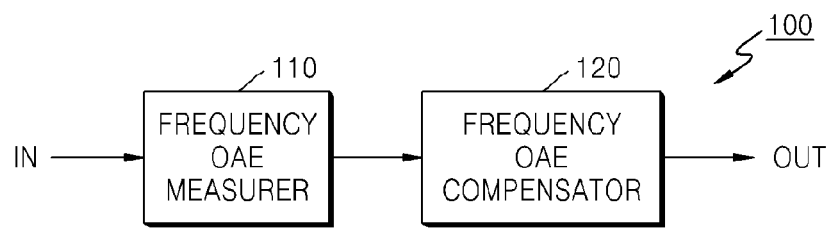
FIG. 1 is a block diagram of an apparatus for measuring an otoacoustic emission (OAE), according to an exemplary embodiment.

FIG. 1 is a block diagram of an apparatus 100 for measuring an otoacoustic emission (OAE), according to an exemplary embodiment. Referring to FIG. 1, the apparatus 100 includes a frequency OAE measurer 110 and a frequency OAE compensator 120.

The frequency OAE measurer 110 measures an OAE value according to frequencies while fixing an input level of a signal and changing a frequency of the signal.

An OAE graph generated by performing frequency sweeping on a signal having a fixed input level will now be referred to as a frequency OAE graph.

The frequency OAE measurer 110 generates the frequency OAE graph with N plot lines, by performing frequency sweeping on N signals having different input levels, wherein N is a natural number of at least 2. The N signals may have regular level intervals, such as 10 dB.

The frequency OAE measurer 110 transmits the frequency OAE graph with the N plot lines to the frequency OAE compensator 120.

The frequency OAE compensator 120 determines whether there are plot lines that overlap each other in the frequency OAE graph. When there are plot lines that overlap each other, the frequency OAE compensator 120 selects a frequency from a frequency section where the plot lines overlap each other, and performs level sweeping on the signal corresponding to the selected frequency.

An OAE graph generated by performing level sweeping on a signal corresponding to a fixed frequency will now be referred to as a level OAE graph. The frequency OAE compensator 120 generates a level OAE graph by performing level sweeping on a signal corresponding to the selected frequency.

The frequency OAE compensator 120 searches for, and compensates for, a section that does not match an auditory characteristic of a person in the level OAE graph. The frequency OAE compensator 120 compensates the frequency OAE graph by using the level OAE graph with the compensated section. Also, the frequency OAE compensator 120 determines a compressed value by using the differences between OAE values of each of the N plot lines in the same frequency.

As such, according to the exemplary embodiment, plot lines that overlap each other are searched for by performing frequency sweeping on signals having a plurality of input levels, and level sweeping is performed on a frequency in a section where the plot lines overlap each other, thereby compensating a frequency OAE graph.

Figure 2:
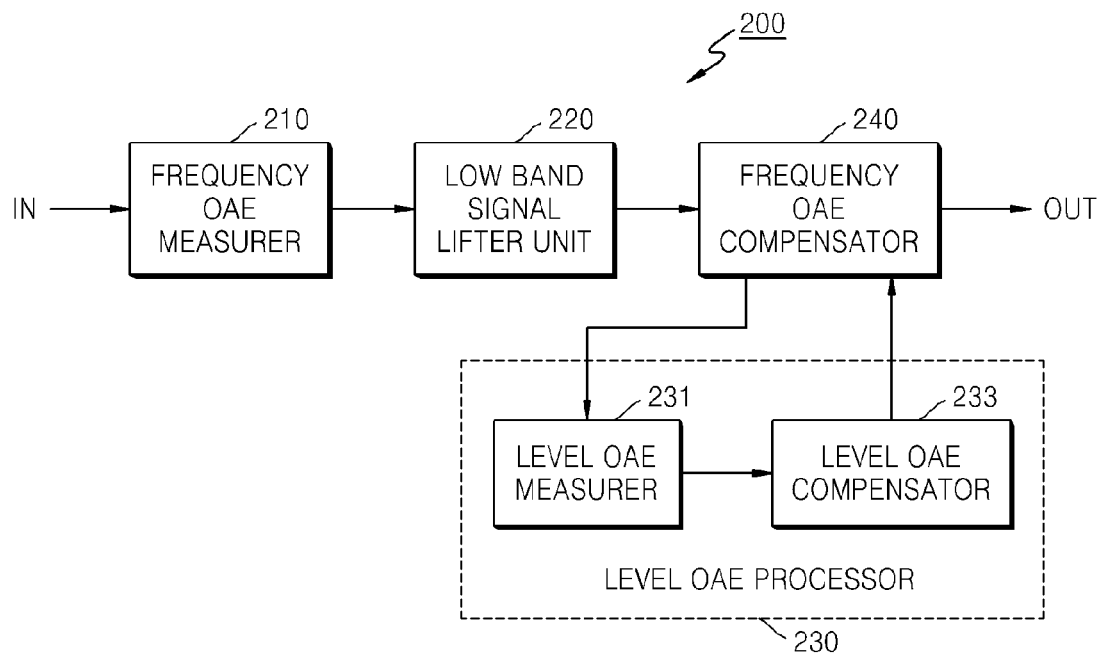
FIG. 2 is a block diagram of an apparatus for measuring an OAE, according to another exemplary embodiment.

FIG. 2 is a block diagram of an apparatus 200 for measuring an OAE, according to another exemplary embodiment. Referring to FIG. 2, the apparatus 200 includes a frequency OAE measurer 210, a low band signal lifter unit 220, a level OAE processor 230, and a frequency OAE compensator 240. Here, the level OAE processor 230 includes a level OAE measurer 231 and a level OAE compensator 233.

The frequency OAE measurer 210 generates a frequency OAE graph with N plot lines by performing frequency sweeping on N signals having different levels, wherein N is a natural number of at least 2. The frequency OAE measurer 210 transmits the frequency OAE graph to the low band signal lifter unit 220.

The low band signal lifter unit 220 lifters a low band signal of the frequency OAE graph with N plot lines in a quefrency domain. Quefrency is used in a cepstrum domain, and corresponds to frequency in a frequency domain. Liftering is a concept in a cepstrum domain and corresponds to filtering in a time or frequency domain. A cepstrum may be a result of taking the Fourier Transform (FT) of a decibel spectrum as if it were a signal.

When only a low band signal is liftered, a component that quickly changes in a signal is removed, and only a component that slowly changes is left. Since not all OAE values are required to measure an auditory sense, the low band signal lifter unit 220 lifters only the low band signal in the quefrency domain, thereby removing insignificant components with respect to auditory characteristics.

The low band signal lifter unit 220 transmits the frequency OAE graph having the liftered low band signal to the frequency OAE compensator 240.

The frequency OAE compensator 240 determines whether there is a section where plot lines overlap each other in the frequency OAE graph. When there is a section where the plot lines overlap each other, the frequency OAE compensator 240 searches for a frequency section in the section where the plot lines overlap each other, and selects one frequency from the frequency section. When there are a plurality of sections where the plot lines overlap each other, the frequency OAE compensator 240 searches for a plurality of frequency sections where the plot lines overlap each other, and selects one frequency from each of the plurality of frequency sections. For description convenience, the frequency selected from the frequency section where the plot lines overlap each other will now be referred to as f0.

According to an exemplary embodiment, the frequency OAE compensator 240 may select a frequency having a middle value from among frequencies in the frequency section as f0. According to another exemplary embodiment, the frequency OAE compensator 240 may select a frequency at a point where a difference between OAE values of the plot lines that overlap each other is the largest, as f0, wherein the point is in the frequency section where the plot lines overlap each other.

The frequency OAE compensator 240 transmits the selected f0 to the level OAE measurer 231. When there are a plurality of frequency sections where the plot lines overlap each other, the frequency OAE compensator 240 transmits the plurality of f0s selected in each frequency section to the level OAE measurer 231.

The level OAE measurer 231 generates a level OAE graph by measuring OAE values according to levels by fixing a frequency of a signal to f0 received from the frequency OAE compensator 240 and changing an input level of the signal. When the plurality of f0s are received from the frequency OAE compensator 240, the level OAE measurer 231 generates the level OAE graph having a plurality of plot lines by performing level sweeping on each of the plurality of f0s.

The level OAE compensator 233 searches for and compensates for an unusual section that is out of a reference pattern, from the level OAE graph generated by the level OAE measurer 231.

Generally, when output levels of OAE are obtained by changing an input level with respect to a fixed frequency, values of the output levels may be constants or a gradient may be linear. The output levels may decrease in spite that the input levels increase because the OAE is offset according to an interaction with other waveforms in a cochlea of an ear, instead of auditory capability of the ear. Accordingly, according to an exemplary embodiment, a section where the output levels of OAE are nonlinear is determined to be the unusual section, and OAE values of the unusual section are compensated for.

The level OAE compensator 233 searches for the unusual section where the output levels are out of the reference pattern in the level OAE graph. In the unusual section, the values of the output levels may not be constants and the gradient of the output level is nonlinear. The level OAE compensator 233 compensates for OAE values of the unusual section according to the reference pattern. The level OAE compensator 233 may compensate for the values of the output levels in the unusual section by using values of output levels around the unusual section. In other words, when the values of the output levels around the unusual section are constants, the values of the output levels in the unusual section are compensated for with constants, and when a gradient of the output levels around the unusual section is linear, the gradient of the output levels in the unusual section may be compensated for to be linear by performing linear interpolation using the values of the output levels around the unusual section. The level OAE compensator 233 transmits the compensated level OAE graph to the frequency OAE compensator 240.

The frequency OAE compensator 240 compensates for the values of the N plot lines in the frequency OAE graph, at the selected f0 by using the compensated level OAE graph. Accordingly, the frequency OAE compensator 240 obtains the values of the N plot lines at the selected f0 by using the compensated level OAE graph. The apparatus 100 or 200 compensates for the values of the N plot lines at the f0 with the obtained values.

The frequency OAE compensator 240 compensates for OAE values of the plot lines in a frequency section that is larger than the frequency section where the plot lines overlap each other by a predetermined size through interpolation, by using OAE values in sections where the plot lines do not overlap each other.

As such, according to the current exemplary embodiment, unnecessary information may be removed by liftering the low band signal of the frequency OAE graph.

Also, when there is the frequency section where the plot lines overlap each other in the OAE graph generated by performing frequency sweeping, a time consumed to measure OAE may be reduced by performing level sweeping only on the selected f0 in the frequency section where the plot lines overlap each other.

In addition, the frequency OAE graph may be compensated by compensating for the unusual section out of the reference pattern in the level OAE graph.

FIG. 3 depicts frequency OAE graphs before liftering a low band signal and after liftering the low band signal, respectively. In both frequency OAE graphs of FIG. 3, a horizontal axis denotes a frequency in Hz and a vertical axis denotes a level of OAE in dB.

The left frequency OAE graph is generated when the frequency OAE measurer 210 of FIG. 2 performs frequency sweeping on one input level. It is seen that a plurality of ripples are included in a plot line of the left frequency OAE graph.

A frequency resolution may not be precise while modeling auditory characteristics of a person. In other words, not all OAE values with respect to all frequencies included in an audible frequency are required, and thus the ripples in the left frequency OAE graph are insignificant in measuring the auditory capability of a person. Accordingly, the low band signal lifter 220 lifters a low band signal in the left frequency OAE graph in a quefrency domain.

The right frequency OAE graph is generated when the low band signal lifter unit 220 lifters the low band signal of the left frequency OAE graph in the quefrency domain. When the low band signal is liftered, a component that quickly changes is removed and only a component that slowly changes is left, and thus a frequency resolution may be decreased. As shown in the right frequency OAE graph of FIG. 3, the ripples are removed, which means that components that are insignificant with respect to auditory characteristics are removed.

As such, according to the current exemplary embodiment, by liftering the low band signal in the frequency OAE graph, the number of operations may be decreased by extracting only information that is necessary with respect to the auditory characteristics.

FIG. 4 depicts OAE graphs that are generated by performing frequency sweeping respectively in an ideal situation and an actual situation.

In both OAE graphs of FIG. 4, a horizontal axis denotes a frequency in Hz and a vertical axis denotes a level of OAE in dB. The left OAE graph shows plot lines that are generated in an ideal situation when OAEs are measured according to frequencies by using three input levels, i.e., 0 dB, 10 dB, and 20 dB. In the left OAE graph, there is no section where the three plot lines overlap each other.

The right OAE graph shows plot lines that are generated by performing frequency sweeping using three different input levels, i.e., a first level, a second level, and a third level. Referring to the right OAE graph of FIG. 4, the plot line generated when the input level is in the second level and the plot line generated when the input level is in the third level overlap each other. A frequency section where the plot lines overlap each other is indicated by R.

According to an exemplary embodiment, when a frequency OAE graph has a frequency section where plot lines overlap each other as shown in the right OAE graph of FIG. 4, values of plot lines in the frequency section where the plot lines overlap each other are compensated for so that the frequency section is removed, as shown in the left OAE graph of FIG. 4.

Accordingly, the apparatus 100 or 200 selects f0 included in the frequency section R where the plot lines overlap each other in the right OAE graph, and performs level sweeping by using the selected f0. The apparatus 100 or 200 compensates a level OAE graph generated through level sweeping, and compensates the right OAE graph of FIG. 4 by using the compensated level OAE graph.

Figure 5:
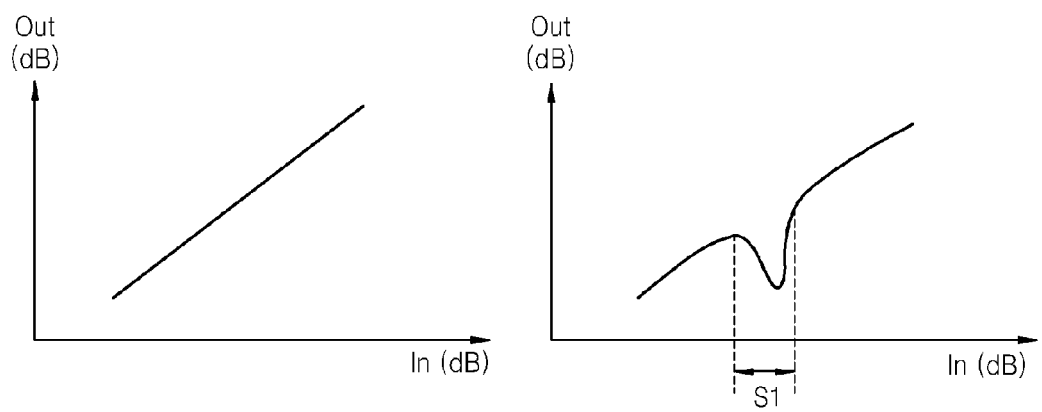
FIGS. 5 and 6 are level OAE graphs that are generated by performing level sweeping when a frequency is fixed.
Figure 6:
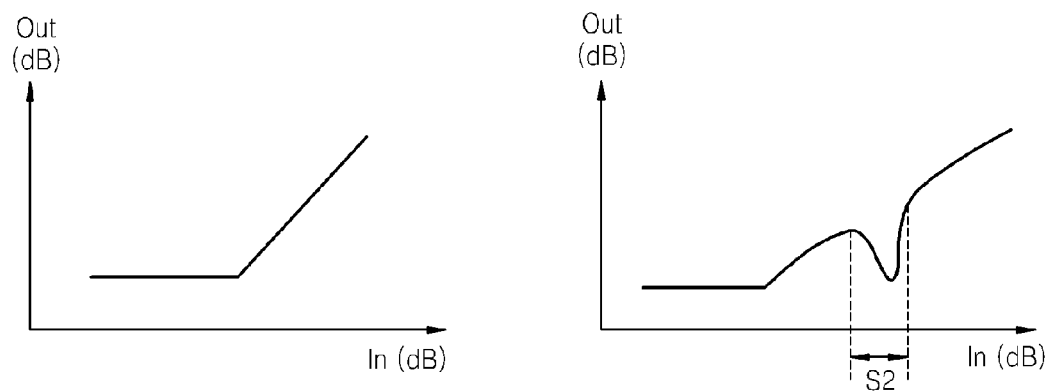

FIGS. 5 and 6 depict level OAE graphs, which are generated by performing level sweeping when a frequency is fixed. In the level OAE graphs of FIGS. 5 and 6, a horizontal axis denotes an input level in dB and a vertical axis denotes a level of OAE in dB, wherein both the horizontal and vertical axis are illustrated in log scale.

The left level OAE graphs according to levels of FIGS. 5 and 6 are generated ideally by performing level sweeping when a frequency is fixed. In other words, when the level sweeping is performed while the frequency is fixed, a gradient may be linear as shown in the left level OAE graph of FIG. 5, or values of a plot line may be constant at first and then a gradient may be linear as shown in the left level OAE graph of FIG. 6.

The right level OAE graphs according to levels of FIGS. 5 and 6 are generated by performing level sweeping on f0 selected from among frequencies in the frequency section R of FIG. 4. Referring to the right level OAE graphs of FIGS. 5 and 6, each plot line includes a nonlinear section in which output levels with respect to the input level are different from a reference pattern. Input levels in the nonlinear sections of the right level OAE graphs of FIGS. 5 and 6 are respectively indicated by S1 and S2.

The apparatus 100 or 200 compensates for values of the output levels in the nonlinear section by using a gradient of output levels in sections around the nonlinear section. In other words, the apparatus 100 or 200 may compensate for the values of the output levels in the input levels S1 and S2 of the nonlinear section by performing linear interpolation using the values of the output levels having a linear gradient around the input levels S1 and S2 where the gradient is nonlinear.

The apparatus 100 or 200 compensates the frequency OAE graph of FIG. 4 by using the compensated level OAE graph.

Figure 7:
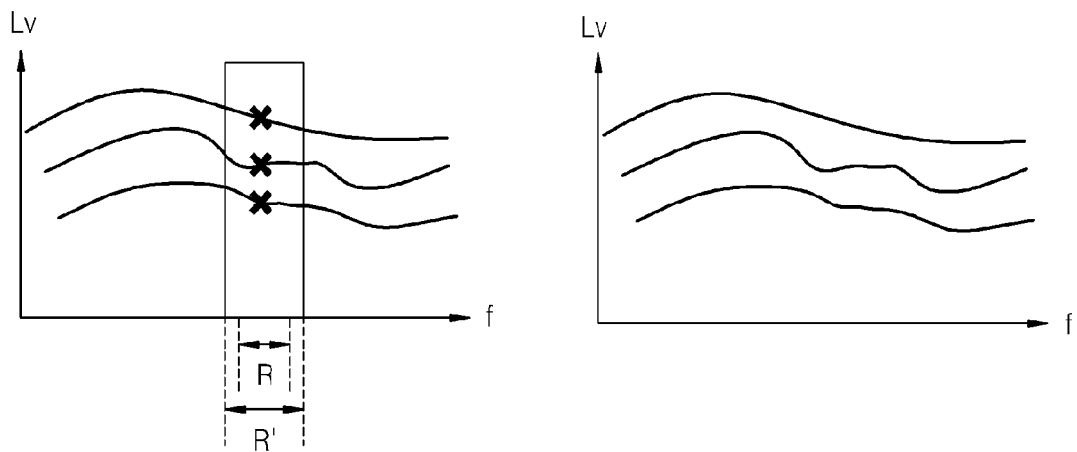
FIG. 7 are graphs for describing the apparatus of FIG. 1 or 2 compensating a frequency OAE graph.

FIG. 7 describes the apparatus 100 or 200 of FIG. 1 or 2. A frequency OAE graph is compensated by using a compensated level OAE graph. In the graphs, a horizontal axis denotes a frequency in Hz and a vertical axis denotes a level of OAE in dB.

The apparatus 100 or 200 compensates for the gradient of the plot line of the input level S1 or S2 in the nonlinear section of the right level OAE graph of FIG. 5 or 6 to be linear, and then compensates the right OAE graph of FIG. 4 to the graph of FIG. 7 by using the compensated right level OAE graph of FIG. 5 or 6. In other words, the apparatus 100 or 200 obtains values of the plot lines in the frequency OAE graph at the f0 frequency selected in the frequency section R, by using the compensated level OAE graph. Then, the apparatus 100 or 200 compensates for the values of the plot lines at the f0 frequency by using the obtained values.

The apparatus 100 or 200 compensates for OAE values in a frequency section larger than the frequency section R, i.e., in a frequency section R' indicated in the left graph of FIG. 7, by using OAE values in frequency sections around the frequency section R'. Also, the apparatus 100 or 200 may obtain a compressed value by using a difference between OAE values in each plot line at the same frequency.

Figure 8:
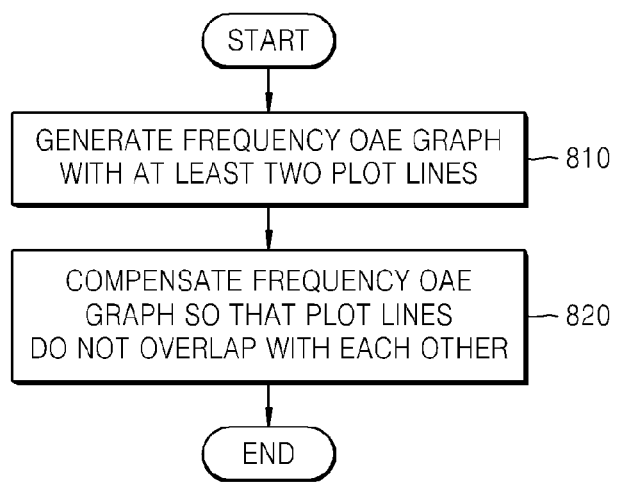
FIG. 8 is a flowchart illustrating a method of measuring an OAE, wherein the method is performed by the apparatus of FIG. 1 or 2, according to an exemplary embodiment.

FIG. 8 is a flowchart illustrating a method of measuring an OAE, wherein the method is performed by the apparatus 100 or 200 of FIG. 1 or 2, according to an exemplary embodiment. Referring to FIG. 8, the OAE apparatus 100 or 200 generates a frequency OAE graph with at least two plot lines in operation 810, while fixing a level of at least two signals. When there is a frequency section where plot lines overlap each other in the generated frequency OAE graph, the apparatus 100 or 200 compensates for the plot lines so that the section is removed in operation 820.

Figure 9:
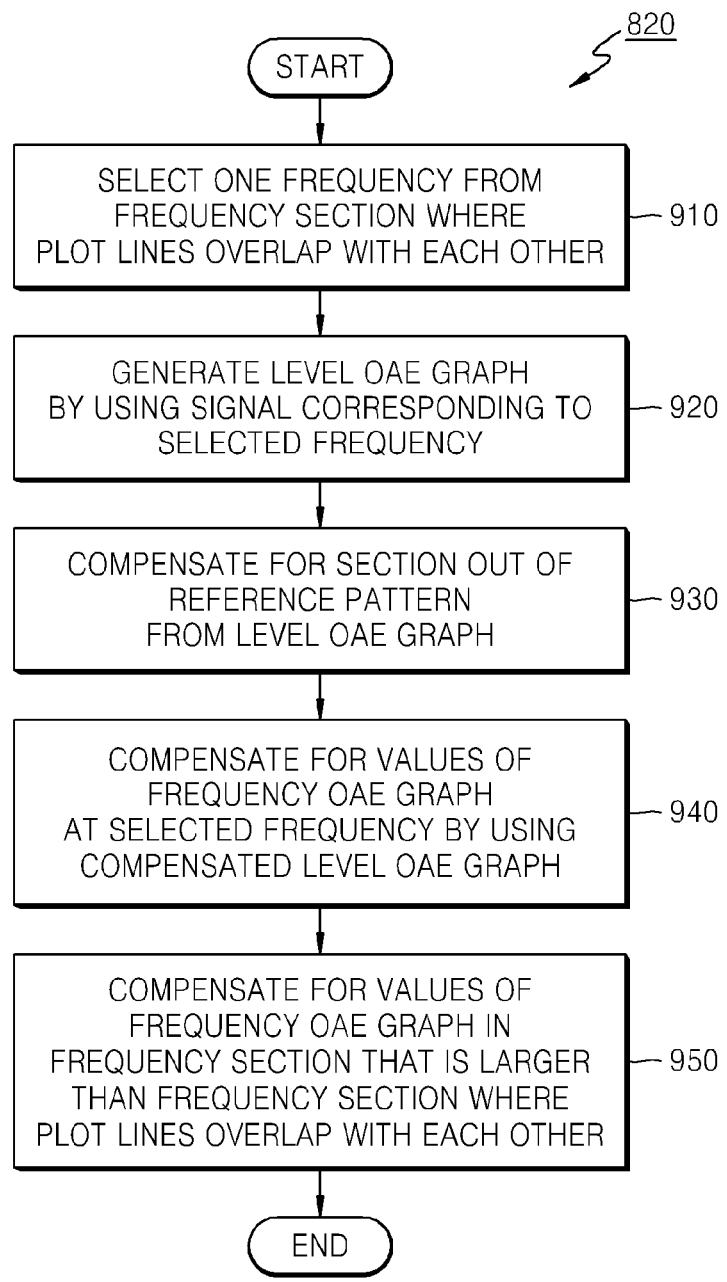
FIG. 9 is a flowchart illustrating operation 820 of FIG. 8 in detail so as to describe a method of processing a signal, according to an exemplary embodiment.

FIG. 9 is a flowchart illustrating operation 820 of FIG. 8 in detail, according to an exemplary embodiment. Referring to FIG. 9, the apparatus 100 or 200 selects one frequency from the frequency section where the plot lines overlap each other, in operation 910.

The apparatus 100 or 200 may select a middle frequency from among the frequencies in the frequency section where the plot lines overlap each other, or a frequency at a point where a difference between OAE values of the plot lines that overlap each other is the largest, wherein the point is in the frequency section where the plot lines overlap each other. When there are a plurality of frequency sections where the plot lines overlap each other, one frequency is selected from each frequency section.

The OAE apparatus 100 or 200 generates a level OAE graph in operation 920, by using a signal corresponding to the selected frequency. When there are frequency sections where the plot lines overlap each other, the level OAE graph includes a plurality of plot lines with respect to the frequencies selected from each frequency section.

The apparatus 100 or 200 searches for a section that is out of a reference pattern from the level OAE graph, and compensates for values of output levels in the section according to the reference pattern, in operation 930. The apparatus 100 or 200 compensates for values of the plot lines in the frequency OAE graph, at the selected frequency by using the compensated level OAE graph, in operation 940. The apparatus 100 or 200 compensates for values of the plot lines of the frequency OAE graph in a frequency section that is larger than the frequency section where the plot lines overlap each other in operation 950, by using an OAE value at the selected frequency and OAE values in sections where the plot lines do not overlap each other.

According to the exemplary embodiments, an OAE may be reliably measured by compensating OAE values in a section where the OAE values remarkably change, by performing frequency sweeping and level sweeping together.

Also, according to the exemplary embodiments, an OAE measuring time may be reduced since unnecessary information is not generated by performing the level sweeping only in the section where the OAE values change remarkably.

The exemplary embodiments can also be embodied as computer readable codes on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, optical data storage devices, etc. The computer readable recording medium can also be distributed over network coupled computer systems so that the computer readable code is stored and executed in a distributed fashion. (Also, functional programs, codes, and code segments for accomplishing the exemplary embodiments can be easily construed by programmers skilled in the art to which the exemplary embodiments pertain.)

While the exemplary embodiments have been particularly shown and described with reference to preferred embodiments thereof, it will be understood by those of ordinary skill in the art that various changes in form and details may be made therein without departing from the spirit and scope of the exemplary embodiments as defined by the appended claims. The exemplary embodiments should be considered in descriptive sense only and not for purposes of limitation. Therefore, the scope of the exemplary embodiments are defined not by the detailed description of the exemplary embodiments but by the appended claims, and all differences within the scope will be construed as being included in the exemplary embodiments.

What is claimed is:

1. A method of compensating an otoacoustic emission (OAE) signal, the method comprising:
receiving the OAE signal generated in an ear of a subject;
generating, by a frequency OAE measurer, a frequency OAE graph with N plot lines corresponding to the received OAE signal, by performing frequency sweeping on N signals having different levels, wherein N is a natural number of at least 2;
when there are plot lines that overlap each other in the frequency OAE graph, compensating values of the N plot lines of the frequency OAE graph in a predetermined frequency section comprising a frequency section where the plot lines overlap each other by performing level sweeping to compensate for a frequency section that does not match an auditory characteristic of a person in the frequency OAE graph; and
outputting signals corresponding to the compensated frequency OAE graph to the subject.

2. The method of claim 1, wherein the N signals have regular level intervals.

3. The method of claim 1, further comprising liftering a low band signal of the frequency OAE graph in a quefrency domain.

4. The method of claim 1, wherein the compensating of the values of the N plot lines comprises:
selecting a frequency in the frequency section where the plot lines overlap each other;
generating a level OAE graph by performing level sweeping on a signal corresponding to the selected frequency;
compensating an OAE value in a section that is out of a reference pattern in the level OAE graph; and
compensating values of the N plot lines of the frequency OAE graph, by using the level OAE graph having the compensated OAE value.

5. The method of claim 4, wherein the selecting of the frequency comprises selecting a middle frequency in the frequency section where the plot lines overlap each other.

6. The method of claim 4, wherein the selecting of the frequency comprises selecting a frequency at a point where a difference between OAE values of the plot lines that overlap each other is the largest, wherein the point is in the frequency section where the plot lines overlap each other.

7. The method of claim 4, wherein the compensating of the values of the N plot lines of the frequency OAE graph by using the level OAE graph having the compensated OAE value comprises:
compensating the values of the N plot lines at the selected frequency by using the level OAE graph having the compensated OAE value; and
compensating OAE values in the predetermined frequency section that is larger than the frequency section where the plot lines overlap each other, by using the values of the N plot lines at the selected frequency.

8. The method of claim 4, wherein the compensating of the OAE value in the section that is out of the reference pattern comprises:
detecting the section that is out of the reference pattern, in the level OAE graph; and
compensating values of a plot line of the level OAE graph in the detected section according to the reference pattern.

9. The method of claim 8, wherein the detecting of the section that is out of the reference pattern comprises detecting a section wherein the values of the plot line of the level OAE graph are not constants and a gradient of the plot line of the level OAE graph is nonlinear.

10. An apparatus for compensating an otoacoustic emission (OAE) signal, the apparatus comprising:
a frequency OAE measurer, configured to receive the OAE signal generated in an ear of a subject and generate a frequency OAE graph with N plot lines corresponding to the received OAE signal, by performing frequency sweeping on N signals having different levels, wherein N is a natural number of at least 2;
a frequency OAE compensator, configured to, when there are plot lines that overlap each other in the frequency OAE graph, compensate values of the N plot lines of the frequency OAE graph in a predetermined frequency section comprises a frequency section where the plot lines overlap each other by performing level sweeping to compensate for a frequency section that does not match an auditory characteristic of a person in the frequency OAE graph, and output signals corresponding to the compensated frequency OAE graph to the subject.

11. The apparatus of claim 10, wherein the N signals have the same level intervals.

12. The apparatus of claim 10, further comprising a low band signal lifter unit which lifters a low band signal of the frequency OAE graph in a quefrency domain.

13. The apparatus of claim 10, wherein the frequency OAE compensator selects a frequency in the frequency section where the plot lines overlap each other, and
the apparatus further comprises:
a level OAE measurer, which generates an level OAE graph by performing level sweeping on a signal corresponding to the selected frequency; and
a level OAE compensator, which compensates for an OAE value in a section that is out of a reference pattern in the level OAE graph,
wherein the frequency OAE compensator compensates for values of the N plot lines of the frequency OAE graph, by using the level OAE graph having the compensated OAE value.

14. The apparatus of claim 13, wherein the frequency OAE compensator selects a middle frequency in the frequency section where the plot lines overlap each other.

15. The apparatus of claim 13, wherein the frequency OAE compensator selects a frequency at a point where a difference between OAE values of the plot lines that overlap each other is the largest, wherein the point is in the frequency section where the plot lines overlap each other.

16. The apparatus of claim 13, wherein the frequency OAE compensator compensates for the values of the N plot lines at the selected frequency, by using the level OAE graph having the compensated OAE value, and compensates for OAE values in the predetermined frequency section that is larger than the frequency section where the plot lines overlap each other, by using the values of the N plot lines at the selected frequency.

17. The apparatus of claim 13, wherein the level OAE compensator detects the section that is out of the reference pattern, in the level OAE graph, and compensates for values of a plot line of the level OAE graph in the detected section according to the reference pattern.

18. The apparatus of claim 17, wherein the level OAE compensator detects a section wherein the values of the plot line of the level OAE graph are not constants and a gradient of the plot line of the level OAE graph is nonlinear.

19. A non-transitory computer readable recording medium having recorded thereon a program for executing a method of compensating an otoacoustic emission (OAE), the method comprising:
   receiving the OAE signal generated in an ear of a subject;
   generating an frequency OAE graph with N plot lines corresponding to the received OAE signal, by performing frequency sweeping on N signals having different levels, wherein N is a natural number of at least 2;
   when there are plot lines that overlap each other in the frequency OAE graph, compensating values of the N plot lines of the frequency OAE graph in a predetermined frequency section comprising a frequency section where the plot lines overlap each other by performing level sweeping to compensate for a frequency section that does not match an auditory characteristic of a person in the frequency OAE graph; and
   outputting signals corresponding to the compensated frequency OAE graph to the subject.

* * * * *